US00PP25379P3

(12) United States Plant Patent
Khemakongkanond

(10) Patent No.: US PP25,379 P3
(45) Date of Patent: Mar. 24, 2015

(54) ***AGLAONEMA* PLANT NAMED 'KKAG201301'**

(50) Latin Name: *Aglaonema commutatum*
Varietal Denomination: KKAG201301

(71) Applicant: Kanachana Khemakongkanond, Bangkok (TH)

(72) Inventor: Kanachana Khemakongkanond, Bangkok (TH)

( * ) Notice: Subject to any disclaimer, the term of this patent is extended or adjusted under 35 U.S.C. 154(b) by 141 days.

(21) Appl. No.: 13/815,762

(22) Filed: Mar. 14, 2013

(65) Prior Publication Data

US 2014/0283268 P1 Sep. 18, 2014

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — Anne Grunberg

(57) ABSTRACT

A new and distinct *Aglaonema* cultivar named 'KKAG201301' is disclosed, characterized by shiny, striking red with green leaf color as well as compact plant size. The new variety is an *Aglaonema*, typically produced as an indoor ornamental plant.

1 Drawing Sheet

Latin name of the genus and species: *Aglaonema commutatum.*

Variety denomination: 'KKAG201301'.

BACKGROUND OF THE INVENTION

The new cultivar is the product of chance discovery. The new variety originated as a naturally occurring whole plant mutation of an, unpatented, proprietary *Aglaonema commutatum* referred to as 'JAY001'.

The new variety was first selected by the inventor, Kanchana Khemakongkanond, a citizen of Thailand, in May of 2009 at a nursery in Bangkok, Thailand. After identifying the new variety as a potentially interesting selection, the inventor continued confidential testing and propagation of 'KKAG201301', assessing stability of the unique characteristics of this variety.

Asexual reproduction of the new cultivar 'KKAG201301' by tissue culture was first performed at a commercial laboratory in Bangkok, Thailand during June of 2010 Subsequently many generations have been produced from tissue cultures and vegetative cuttings, and have shown that the unique features of this cultivar are stable and reproduced true to type.

SUMMARY OF THE INVENTION

The cultivar 'KKAG201301' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKAG201301'. These characteristics in combination distinguish 'KKAG201301' as a new and distinct *Aglaonema* cultivar:

1. Striking red with green leaf color.
2. Compact plant size.
3. Shiny leaf appearance.

PARENT COMPARISON

Plants of the new cultivar 'KKAG201301' are similar to the parent variety in most horticultural characteristics. The new cultivar, however, produces longer, pointier, and narrower leaves than the seed parent. Additionally the new cultivar produces a leaf with a shinier appearance than foliage of the parent.

COMMERCIAL COMPARISON

Plants of the new cultivar 'KKAG201301' are comparable to the unpatented variety *Aglaonema* 'Unyamanee Red'. The two *Aglaonema* varieties are similar in most horticultural characteristics; however, the new variety 'KKAG201301' produces leaves that are smaller, narrower and of different shape than those of comparator 'Unyamanee Red'. The leaves of 'KKAG201301' produce more red coloration than those of comparator 'Unyamanee Red'.

Plants of the new cultivar 'KKAG201301' can also be compared to the unpatented variety *Aglaonema* 'Christmas Day'. The two *Aglaonema* varieties are similar in most horticultural characteristics; however, the new variety 'KKAG201301' produces leaves of a different shape than those of comparator 'Christmas Day'. The leaves of 'KKAG201301' produce more red coloration than those of comparator 'Christmas Day'.

BRIEF DESCRIPTION OF THE PHOTOGRAPH

The accompanying photograph in FIG. 1 illustrates in full color a typical plant of 'KKAG201301' grown in a commercial greenhouse in Honselersdijk, the Netherlands. This plant is approximately 8 months old shown planted in 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KKAG201301' plants grown according to the following protocols.

Plants were grown in Honselersdijk, the Netherlands under controlled greenhouse conditions, with temperatures ranging approximately from 20° C. to 22° C. during the day and 18° C. to 20° C. at night with natural sunlight. Measurements and numerical values below represent averages of typical plant types.

Botanical classification: *Aglaonema commutatum* 'KKAG201301'.

PROPAGATION

Propagation details:
First propagation method: Cuttings.
Type of propagation typically used: Cuttings.
Time to initiate roots: About 14 days at approximately 21° C.
Root description: Moderately dense, moderately thick, non-fibrous, fleshy, not free-branched, colored greyed-orange; near RHS-CC 165C.
Time to produce rooted plantlet: Approximately 10 weeks at approximately 20 to 22° C.

PLANT

Age of plant described: Approximately 8 months.
Growth habit: Broad upright.
Plant shape: Broad obovate, top flattened.
Height: Approximately 12.7 cm to top of highest leaf.
Plant spread: Approximately 20.5 cm in a 12 cm circular pot.
Normal pot size: 12 cm circular pot.
Growth rate: Slow to moderate.
Stem:
- *Diameter.*—0.7 cm.
- *Length.*—4.3 cm.
- *Color.*—Yellow-green; near RHS 146A.
- *Texture.*—Smooth, moderately glossy.

Branching characteristics: Basal branching, no lateral branches.
Number of clumps of leaves: 2.
Number of leaves per clump: Average 13.
Number of leaves per plant: Approximately 26.

FOILAGE

Leaf:
- *Arrangement.*—Irregular basal emerging.
- *Average length (excluding petiole).*—Approximately 8.7 cm.
- *Average width.*—Approximately 3.8 cm.
- *Shape of blade.*—Ovate.
- *Angle of growth.*—Leaves outward (near horizontal) to very slightly upright.
- *Aspect.*—Slightly undulating.
- *Apex.*—Long apiculate.
- *Base.*—Rounded.
- *Margin.*—Entire.
- *Appearance.*—Upper surface glossy, lower surface slightly glossy.
- *Texture of top surface.*—Smooth.
- *Texture of bottom surface.*—Smooth.
- *Color.*—Young foliage upper side: Red; near RHS 53D, lighter towards the base; near RHS 54B, narrow and irregular margins and blotches green to yellow-green; near RHS N137A and 147A. Young foliage under side: Red; near RHS 51C, narrow and irregular margins and blotches green to yellow-green; near RHS N137A and 147A. Mature foliage upper side: Red; near RHS 53B, lighter towards the base; near RHS 53C, irregular blotches and margins green to yellow-green; near RHS 139A and 144B. Mature foliage under side: Red to greyed-red; in between near RHS 150D and 181D irregular blotches and margins green; near RHS N137A and 143C.

Venation:
- *Type.*—Pinnate.
- *Venation coloration upper side.*—Greyed-purple; near RHS 183C.
- *Venation coloration under side.*—Green; near RHS 143A and 143B.

Sheath:
- *Average length.*—Approximately 3.0 cm.
- *Average width.*—Approximately 0.4 cm.
- *Color.*—Yellow-Green; near RHS 144C and 145D.
- *Texture.*—Smooth.
- *Appearance.*—Matte.

Immature petiole:
- *Length.*—Approximately 4.2 cm.
- *Width.*—At distal end: Approximately 0.2 cm. Above clump: Approximately 0.5 cm.
- *Color.*—Green; near RHS 137D, more towards yellow-green near the base; near RHS 143A to 143B.
- *Strength.*—Strong.

Mature petiole:
- *Length.*—Approximately 6.8 cm.
- *Width.*—At distal end: Approximately 0.5 cm. Above clump: Approximately 0.9 cm.
- *Color.*—Green-white; near RHS 157D.
- *Strength.*—Strong.

Geniculum: No geniculum observed.

FLOWERING CHARACTERISTICS

Flowering not observed to date.

REPRODUCTIVE ORGANS

Not observed to date.

OTHER CHARACTERISTICS

Disease resistance: Good resistance to the normal diseases found in *Aglaonema.*
Drought tolerance and cold tolerance: Normal for species, USDA zone 10 and higher.
Fruit/seed production: No fruits/seeds detected to date.

What is claimed is:

1. A new and distinct cultivar of *Aglaonema* plant named 'KKAG201301' as herein illustrated and described.

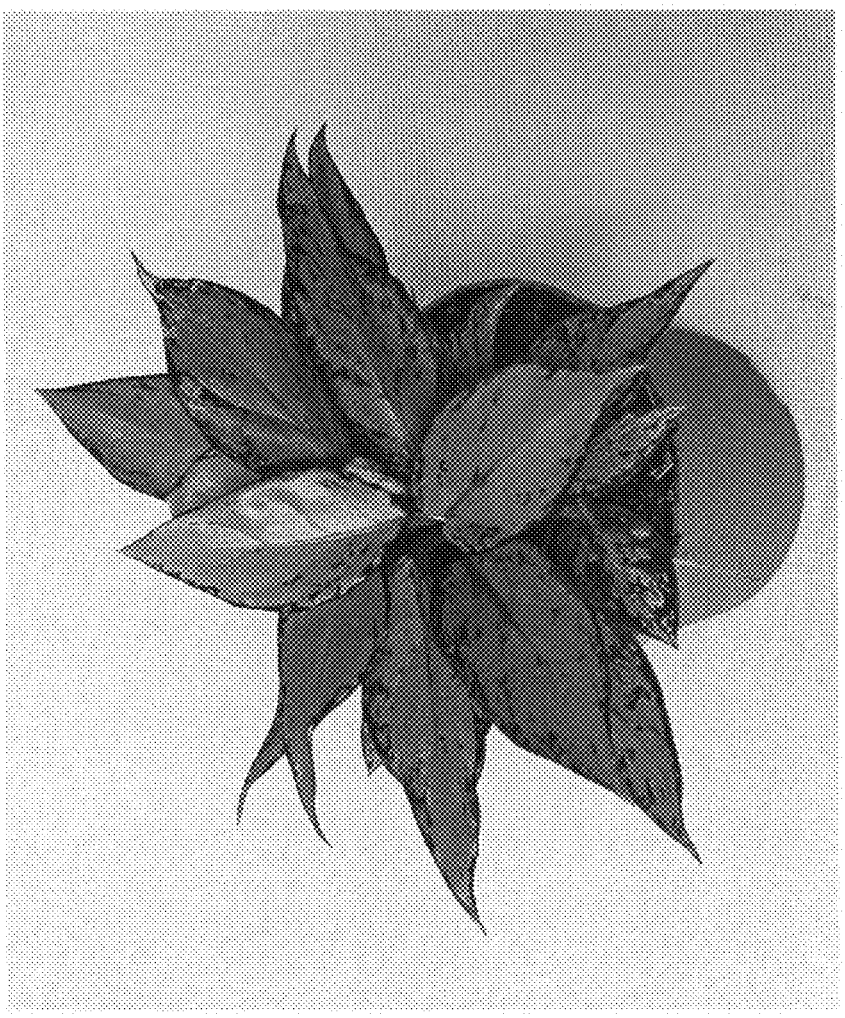

* * * * *